US008152843B2

(12) United States Patent
Williams et al.

(10) Patent No.: US 8,152,843 B2
(45) Date of Patent: Apr. 10, 2012

(54) POLYMERIC ENDOPROSTHESIS AND METHOD OF MANUFACTURE

(75) Inventors: Michael S. Williams, Santa Rosa, CA (US); Kevin D. Holbrook, Chapel Hill, NC (US); Richard A. Glenn, Santa Rosa, CA (US); Jeffrey A. Smith, Petaluma, CA (US); Joseph M. DeSimone, Chapel Hill, NC (US)

(73) Assignee: SyneCor, LLC, Durham, NC (US)

( * ) Notice: Subject to any disclaimer, the term of this patent is extended or adjusted under 35 U.S.C. 154(b) by 366 days.

(21) Appl. No.: 12/215,493

(22) Filed: Jun. 26, 2008

(65) Prior Publication Data
US 2008/0275539 A1    Nov. 6, 2008

Related U.S. Application Data

(62) Division of application No. 10/342,748, filed on Jan. 15, 2003, now abandoned.

(60) Provisional application No. 60/426,898, filed on Nov. 15, 2002, provisional application No. 60/426,737, filed on Nov. 15, 2002, provisional application No. 60/426,734, filed on Nov. 15, 2002, provisional application No. 60/426,126, filed on Nov. 14, 2002, provisional application No. 60/426,125, filed on Nov. 14, 2002.

(51) Int. Cl.
*A61F 2/06*      (2006.01)

(52) U.S. Cl. ............... 623/1.32; 623/1.38; 623/1.49
(58) Field of Classification Search .................. None
See application file for complete search history.

(56) References Cited

U.S. PATENT DOCUMENTS

| 5,622,188 A * | 4/1997 | Plaia et al. ............ 128/898 |
| 5,824,049 A * | 10/1998 | Ragheb et al. ............ 623/1.44 |
| 6,287,332 B1 * | 9/2001 | Bolz et al. ............ 623/1.15 |
| 6,409,750 B1 | 6/2002 | Hyodoh |
| 6,752,826 B2 * | 6/2004 | Holloway et al. ............ 623/1.13 |
| 2002/0004060 A1 * | 1/2002 | Heublein et al. ............ 424/422 |
| 2002/0099438 A1 * | 7/2002 | Furst ............ 623/1.16 |

FOREIGN PATENT DOCUMENTS

DE      101 05 592 A1    8/2002

* cited by examiner

*Primary Examiner* — David H Willse
*Assistant Examiner* — Javier Blanco
(74) *Attorney, Agent, or Firm* — Deanna Shirley Williams

(57) ABSTRACT

Improved polymeric endoprostheses having reinforcement elements and methods of making the endoprostheses are disclosed. The devices disclosed exhibit improved overall compliance, selective regional compliance, and selective radial strength without varying the geometries of selected regions. Numerous other physical characteristics of the endoprostheses described may be selectively varied during manufacture. Some embodiments may include an erodible polymer and magnesium. Some embodiments may have one or more therapeutics incorporated into the endoprosthesis via a solvent in a supercritical state.

1 Claim, 24 Drawing Sheets

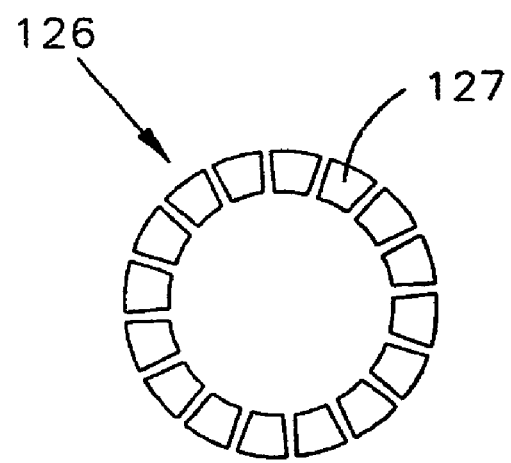
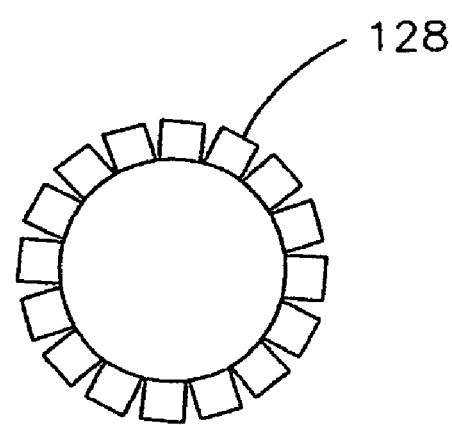
FIG. 10A
FIG. 10B
PRIOR ART

POLYMERIC ENDOPROSTHESIS AND METHOD OF MANUFACTURE

RELATED APPLICATIONS

This application is a divisional of U.S. patent application Ser. No. 10/342,748 filed Jan. 15, 2003 by Williams, et al., entitled "Polymeric Endoprosthesis and Method of Manufacture", now abandoned.

This application is related to Provisional U.S. Patent Application Ser. No. 60/426,898, filed Nov. 15, 2002, entitled "Polymeric Endoprostheses and Methods of Manufacture", to Williams, et al., Provisional U.S. Patent Application Ser. No. 60/426,737, filed Nov. 15, 2002, entitled "Improved Endoprostheses and Methods of Manufacture", to Williams, et al., Provisional U.S. Patent Application Ser. No. 60/426,734, filed Nov. 15, 2002, entitled "Photocurable Endoprostheses and Methods of Manufacture", to Williams et al., Provisional U.S. Patent Application Ser. No. 60/426,126, filed Nov. 14, 2002, entitled "Carbon Dioxide-Assisted Methods of Providing Biocompatible Intraluminal Prostheses", to Williams, et al., and Provisional U.S. Patent Application Ser. No. 60/426,125, filed Nov. 14, 2002, entitled "Intraluminal Prostheses and Carbon Dioxide-Assisted Methods of Impregnating Same with Pharmacological Agents" to Williams, et al.". The above applications are commonly owned. All of the above applications are hereby incorporated by reference, each in its entirety.

FIELD OF THE INVENTION

The invention herein relates generally to medical devices and the manufacture thereof, and to improved endoprostheses for use in the treatment of strictures in lumens of the body. More particularly, the invention is directed to polymeric endoprostheses and addresses the shortcomings of the prior art, especially, but not limited to, material limitations including radial strength and elastic recoil.

BACKGROUND OF THE INVENTION

Ischemic heart disease is the major cause of death in industrialized countries. Ischemic heart disease, which often results in myocardial infarction, is a consequence of coronary atherosclerosis. Atherosclerosis is a complex chronic inflammatory disease and involves focal accumulation of lipids and inflammatory cells, smooth muscle cell proliferation and migration, and the synthesis of extracellular matrix. *Nature* 1993; 362:801-809. These complex cellular processes result in the formation of atheromatous plaque, which consists of a lipid-rich core covered with a collagen-rich fibrous cap, varying widely in thickness. Further, plaque disruption is associated with varying degrees of internal hemorrhage and luminal thrombosis because the lipid core and exposed collagen are thrombogenic. *J Am Coll Cardiol.* 1994; 23:1562-1569 Acute coronary syndrome usually occurs as a consequence of such disruption or ulceration of a so called "vulnerable plaque". *Arterioscler Thromb Vasc Biol.* Volume 22, No. 6, June 2002, p. 1002.

In addition to coronary bypass surgery, a current treatment strategy to alleviate vascular occlusion includes percutaneous transluminal coronary angioplasty, expanding the internal lumen of the coronary artery with a balloon. Roughly 800,000 angioplasty procedures are performed in the U.S. each year (*Arteriosclerosis, Thrombosis, and Vascular Biology* Volume 22, No. 6, June 2002, p. 884). However, 30% to 50% of angioplasty patients soon develop significant restenosis, a narrowing of the artery through migration and growth of smooth muscle cells.

In response to the significant restenosis rate following angioplasty, percutaneously placed endoprostheses have been extensively developed to support the vessel wall and to maintain fluid flow through a diseased coronary artery. Such endoprostheses, or stents, which have been traditionally fabricated using metal alloys, include self-expanding or balloon-expanded devices that are "tracked" through the vasculature and deployed proximate one or more lesions. Stents considerably enhance the long-term benefits of angioplasty, but 10% to 50% of patients receiving stents still develop restenosis. (*J Am Coll Cardiol.* 2002; 39:183-193. Consequently, a significant portion of the relevant patient population undergoes continued monitoring and, in many cases, additional treatment.

Continued improvements in stent technology aim at producing easily tracked, easily visualized and readily deployed stents, which exhibit the requisite radial strength without sacrificing a small delivery profile and sufficient flexibility to traverse the diseased human vasculature. Further, numerous therapies directed to the cellular mechanisms of accumulation of inflammatory cells, smooth muscle cell proliferation and migration show tremendous promise for the successful long-term treatment of ischemic heart disease. Consequently, advances in coupling delivery of such therapies to the mechanical support of vascular endoprostheses, delivered proximate the site of disease, offer great hope to the numerous individuals suffering heart disease.

While advances in the understanding of ischemic heart disease as a complex chronic inflammatory process take place, traditional diagnostic techniques such as coronary angiography yield to next generation imaging modalities. In fact, coronary angiography may not be at all useful in identifying inflamed atherosclerotic plaques that are prone to producing clinical events. Imaging based upon temperature differences, for example, are undergoing examination for use in detecting coronary disease. Magnetic resonance imaging (MRI) is currently emerging as the state of the art diagnostic for arterial imaging, enhancing the detection, diagnosis and monitoring of the formation of vulnerable plaques. Transluminal intervention guided by MRI is expected to follow. However, metals produce distortion and artifacts in MR images, rendering use of the traditionally metallic stents in coronary, biliary, esophageal, ureteral, and other body lumens incompatible with the use of MRI.

Consequently, an emerging clinical need for interventional devices that are compatible with and complementary to new imaging modalities is evident. Further, devices that exhibit improved trackability to previously undetectable disease within remote regions of the body, especially the coronary vasculature are needed. And finally, devices that both exhibit improved mechanical support and are readily compatible with adjunct therapies in order to lower or eliminate the incidence of restenosis are needed.

SUMMARY OF THE INVENTION

An endoprosthesis is provided comprising one or more erodible materials, a first region and a second region, wherein said first region comprises a first degree of overall compliance and said second region comprises a second degree of overall compliance, wherein said first degree of overall compliance is greater than said second degree, whereby when said endoprosthesis is disposed within a body lumen comprising walls comprising irregular morphology, said first region is substantially compliant with said walls. In some embodiments, the greater compliance is proximate one or both ends of the endoprosthesis. Alternatively, the connecting members of an endoprosthesis may be more compliant according to the invention. The improved compliance can be attained without altering the cross section or geometry of the endoprosthesis. Radial conformability, axial flexibility, linear extensibility, outward radial force, density, crystallinity, permeability and diffusion coefficient can all be altered according to the invention. In some embodiments according to the invention, the endoprosthesis elements comprise a trapezoidal cross section, narrowed apices, a metal reinforcing element, one or more therapeutic agents. Some embodiments according to the invention comprise an expandable endoprosthesis comprising poly-lactic acid and polycaprolactone in a ratio of between 80:20 and 95:5. The endoprosthesis may further be is annealed at a temperature of between 50 and 200 degrees C. for a duration of between one half and 24 hours, and may additionally undergo strain induced crystallization upon expansion.

An endoprosthesis according to the invention may comprise and endoprosthesis element comprising a plurality of apices alternating with a plurality of straight sections wherein said endoprosthesis undergoes strain induced crystallization upon expansion proximate the apices. Methods of manufacturing endoprostheses according to the invention are also disclosed.

BRIEF DESCRIPTION OF THE DRAWINGS

FIG. 10A is an end view of a cross section of an embodiment according to the invention.

FIG. 10B is an end view of a cross section of an endoprosthesis of the prior art.

DETAILED DESCRIPTION OF THE INVENTION

Figure 1:
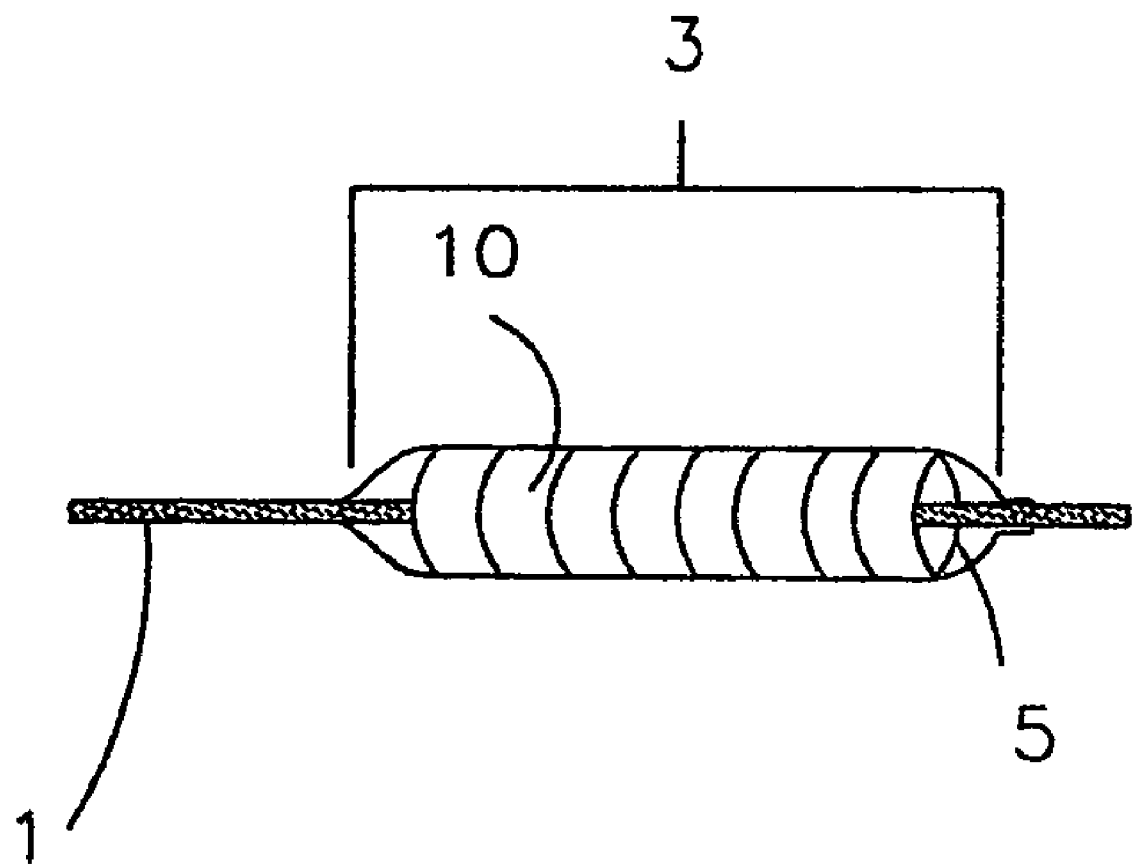
FIG. 1 is a plan view of the distal end of a conventional balloon catheter having a stent according to the invention mounted thereon.

Although the invention herein is not limited as such, some embodiments of the invention comprise materials that are bioerodible. "Erodible" refers to the ability of a material to maintain its structural integrity for a desired period of time, and thereafter gradually undergo any of numerous processes whereby the material substantially loses tensile strength and mass. Examples of such processes comprise hydrolysis, enzymatic and non-enzymatic degradation, oxidation, enzymatically-assisted oxidation, and others, thus including bioresorption, dissolution, and mechanical degradation upon interaction with a physiological environment into components that the patient's tissue can absorb, metabolize, respire, and/or excrete. Polymer chains are cleaved by hydrolysis and are eliminated from the body through the Krebs cycle, primarily as carbon dioxide and in urine. "Erodible" and "degradable" are intended to be used interchangeably herein.

The term "endoprosthesis" refers to any prosthetic device placed within a body lumen or duct to in order to therapeutically treat the body lumen or duct, including but not limited to the objective of restoring or enhancing flow of fluids through a body lumen or duct.

A "self-expanding" endoprosthesis has the ability to revert readily from a reduced profile configuration to a larger profile configuration in the absence of a restraint upon the device that maintains the device in the reduced profile configuration.

"Balloon expandable" refers to a device that comprises a reduced profile configuration and an expanded profile configuration, and undergoes a transition from the reduced configuration to the expanded configuration via the outward radial force of a balloon expanded by any suitable inflation medium.

The term "balloon assisted" refers to a self-expanding device the final deployment of which is facilitated by an expanded balloon.

The term "fiber" refers to any generally elongate member fabricated from any suitable material, whether polymeric, metal or metal alloy, natural or synthetic.

The phrase "points of intersection", when used in relation to fiber(s), refers to any point at which a portion of a fiber or two or more fibers cross, overlap, wrap, pass tangentially, pass through one another, or come near to or in actual contact with one another.

As used herein, a device is "implanted" if it is placed within the body to remain for any length of time following the conclusion of the procedure to place the device within the body.

The term "diffusion coefficient" refers to the rate by which a substance elutes, or is released either passively or actively from a substrate.

As used herein, the term "braid" refers to any braid or mesh or similar woven structure produced from between 1 and several hundred longitudinal and/or transverse elongate elements woven, braided, knitted, helically wound, or intertwined by any manner, at angles between 0 and 180 degrees and usually between 45 and 105 degrees, depending upon the overall geometry and dimensions desired.

Unless specified, suitable means of attachment may include by thermal melt, chemical bond, adhesive, sintering, welding, or any means known in the art.

"Shape memory" refers to the ability of a material to undergo structural phase transformation such that the material may define a first configuration under particular physical and/or chemical conditions, and to revert to an alternate configuration upon a change in those conditions. Shape memory materials may be metal alloys including but not limited to nickel titanium, or may be polymeric. A polymer is a shape memory polymer if the original shape of the polymer is recovered by heating it above a shape recovering temperature (defined as the transition temperature of a soft segment) even if the original molded shape of the polymer is destroyed mechanically at a lower temperature than the shape recovering temperature, or if the memorized shape is recoverable by application of another stimulus. Such other stimulus may include but is not limited to pH, salinity, hydration, and others.

As used herein, the term "segment" refers to a block or sequence of polymer forming part of the shape memory polymer. The terms hard segment and soft segment are relative terms, relating to the transition temperature of the segments. Generally speaking, hard segments have a higher glass transition temperature than soft segments, but there are exceptions. Natural polymer segments or polymers include but are not limited to proteins such as casein, gelatin, gluten, zein, modified zein, serum albumin, and collagen, and polysaccharides such as alginate, chitin, celluloses, dextrans, pullulane, and polyhyaluronic acid; poly(3-hydroxyalkanoate)s, especially poly(.beta.-hydroxybutyrate), poly(3-hydroxyoctanoate) and poly(3-hydroxyfatty acids).

Representative natural erodible polymer segments or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyorthoesters, polyvinyl ethers, polyvinyl esters, polyvinyl halides, polyvinylpyrrolidone, polyesters, polylactides, polyglycolides, polysiloxanes, polyurethanes and copolymers thereof.

Examples of suitable polyacrylates include poly(methyl methacrylate); poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, arboxymethyl cellulose, cellulose triacetate and cellulose sulfate sodium salt. These are collectively referred to herein as "celluloses".

Examples of synthetic degradable polymer segments or polymers include polyhydroxy acids, polylactides, polyglycolides and copolymers thereof, poly(ethylene terephthalate), poly(hydroxybutyric acid), poly(hydroxyvaleric acid), poly[lactide-co-(epsilon-caprolactone)], poly[glycolide-co-(epsilon-caprolactone)], polycarbonates, poly-(epsilon caprolactone) poly(pseudo amino acids), poly(amino acids), poly(hydroxyalkanoate)s, polyanhydrides, polyorthoesters, and blends and copolymers thereof.

The degree of crystallinity of the polymer or polymeric block(s) is between 3 and 80%, more often between 3 and 65%. The tensile modulus of the polymers below the transition temperature is typically between 50 MPa and 2 GPa (gigapascals), whereas the tensile modulus of the polymers above the transition temperature is typically between 1 and 500 MPa.

The melting point and glass transition temperature of the hard segment are generally at least 10 degrees C., and preferably 20 degrees C., higher than the transition temperature of the soft segment. The transition temperature of the hard segment is preferably between −60 and 270 degrees C., and more often between 30 and 150 degrees C. The ratio by weight of the hard segment to soft segments is between about 5:95 and 95:5, and most often between 20:80 and 80:20. The polymers contain at least one physical crosslink (physical interaction of the hard segment) or contain covalent crosslinks instead of a hard segment. Polymers can also be interpenetrating networks or semi-interpenetrating networks.

Rapidly erodible polymers such as poly(lactide-co-glycolide)s, polyanhydrides, and polyorthoesters, which have carboxylic groups exposed on the external surface as the smooth surface of the polymer erodes, also can be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Examples of suitable hydrophilic polymers include but are not limited to poly(ethylene oxide), polyvinyl pyrrolidone, polyvinyl alcohol, poly(ethylene glycol), polyacrylamide poly(hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof.

Hydrogels can be formed from polyethylene glycol, polyethylene oxide, polyvinyl alcohol, polyvinyl pyrrolidone, polyacrylates, poly(ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of melting even when the polymers are not hydrated. Either type of polymeric block can be used, depending on the desired application and conditions of use.

The use of polymeric materials in the fabrication of endoprostheses confers the advantages of improved flexibility, compliance and conformability, permitting treatment in body lumens not accessible by more conventional endoprostheses. Such advantages over a more conventional metal alloy are most readily apparent in an endoprosthesis comprising longitudinal connecting members, for example. Such connecting members, when fabricated from one or more polymeric materials, allow compression of the connecting member under compression loads, or, alternatively, stretching under tension, while maintaining axial stability. In addition, more connecting members at more points on the endoprosthesis can be utilized, stabilizing the device without rendering the device overly rigid.

Fabrication of an endoprosthesis according to the invention allows for the use of different materials in different regions of the prosthesis to achieve different physical properties as desired for a selected region. A material selected for its ability to allow elongation of longitudinal connecting members on the outer radius of a curve in a lumen, and compression on the inner radius of a curve in a vessel allows improved tracking of a device through a diseased lumen. A distinct material may be selected for support elements in order that the support elements exhibit sufficient radial strength. Further, the use of polymeric materials readily allows for the fabrication of endoprostheses comprising transitional end portions with greater compliance than the remainder of the prosthesis, thereby minimizing any compliance mismatch between the endoprosthesis and diseased lumen. Further, a polymeric material can uniformly be processed to fabricate a device exhibiting better overall compliance with a pulsating vessel, which, especially when diseased, typically has irregular and often rigid morphology. Trauma to the vasculature, for example, is thereby minimized, reducing the incidence of restenosis that commonly results from vessel trauma.

An additional advantage of polymers includes the ability to control and modify properties of the polymers through the use a variety of techniques. According to the invention, optimal ratios of combined polymers, and optimal processing have been found to achieve highly desired properties not typically found in polymers. Polymers such as poly-1-lactic acid and poly-caprolactone, combined in ratios of between 80:20 and 95:5 respectively, form materials exhibiting a desirable modulus of elasticity. Further, the annealing process (comprising heating of the materials according chosen parameters including time and temperature) increases polymer chain crystallization, thereby increasing the strength of the material. Consequently, according to the invention, the desired material properties can be achieved by using the appropriate ratio of materials and by annealing the materials.

Additionally, the properties of polymers can be enhanced and differentiated by controlling the degree to which the material crystallizes through strain-induced crystallization. Means for imparting strain-induced crystallization are enhanced during deployment of an endoprosthesis according to the invention. Upon expansion of an endoprosthesis according to the invention, focal regions of plastic deformation undergo strain-induced crystallization, further enhancing the desired mechanical properties of the device, such as further increasing radial strength. The strength is optimized when the endoprosthesis is induced to bend preferentially at desired points, and the included angle of the endoprosthesis member is between 40 and 70 degrees.

Curable materials employed in the fabrication of some of the embodiments herein include any material capable of being able to transform from a fluent or soft material to a harder material, by cross-linking, polymerization, or other suitable process. Materials may be cured over time, thermally, chemically, or by exposure to radiation. For those materials that are cured by exposure to radiation, many types of radiation may be used, depending upon the material. Wavelengths in the spectral range of about 100-1300 nm may be used. The material should absorb light within a wavelength range that is not readily absorbed by tissue, blood elements, physiological fluids, or water. Ultraviolet radiation having a wavelength ranging from about 100-400 nm may be used, as well as visible, infrared and thermal radiation. The following materials are examples of curable materials: urethanes, poly- urethane oligomer mixtures, acrylate monomers, aliphatic urethane acrylate oligomers, acrylamides, UV polyanhydrides, UV curable epoxies, and other UV curable monomers. Alternatively, the curable material can be a material capable of being chemically cured, such as silicone based compounds which undergo room temperature vulcanization.

Some embodiments according to the invention comprise materials that are cured in a desired pattern. Such materials may be cured by any of the foregoing means. Further, for those materials that are photocurable, such a pattern may be created by coating the material in a negative image of the desired pattern with a masking material using standard photoresist technology. Absorption of both direct and incident radiation is thereby prevented in the masked regions, curing the device in the desired pattern. A variety of biocompatibly eroding coating materials may be used, including but not limited to gold, magnesium, aluminum, silver, copper, platinum, inconel, chrome, titanium indium, indium tin oxide. Projection optical photolithography systems that utilize the vacuum ultraviolet wavelengths of light below 240 nm provide benefits in terms of achieving smaller feature dimensions. Such systems that utilize ultraviolet wavelengths in the 193 nm region or 157 nm wavelength region have the potential of improving precision masking devices having smaller feature sizes.

An endoprosthesis comprising polymeric materials has the additional advantage of compatibility with magnetic resonance imaging, potentially a long term clinical benefit. Further, if the more conventional diagnostic tools employing angiography continue as the technique of choice for delivery and monitoring, radiopacity can be readily conferred upon polymeric materials.

Though not limited thereto, some embodiments according to the invention comprise one or more therapeutic substances that will elute from the surface or the structure or prosthesis independently or as the prosthesis erodes. The cross section of an endoprosthesis member may be modified according to the invention in order to maximize the surface area available for delivery of a therapeutic from the vascular surface of the device. A trapezoidal geometry will yield a 20% increase in surface area over a rectangular geometry of the same cross-sectional area. In addition, the diffusion coefficient and/or direction of diffusion of various regions of an endoprosthesis, surface, may be varied according to the desired diffusion coefficient of a particular surface. Permeability of the luminal surface, for example, may be minimized, and diffusion from the vascular surface maximized, for example, by altering the degree of crystallinity of the respective surfaces.

According to the invention, such surface treatment and/or incorporation of therapeutic substances may be performed utilizing one or more of numerous processes that utilize carbon dioxide fluid, e.g., carbon dioxide in a liquid or supercritical state. A supercritical fluid is a substance above its critical temperature and critical pressure (or "critical point"). Compressing a gas normally causes a phase separation and the appearance of a separate liquid phase. However, all gases have a critical temperature above which the gas cannot be liquefied by increasing pressure, and a critical pressure or pressure which is necessary to liquefy the gas at the critical temperature. For example, carbon dioxide in its supercritical state exists as a form of matter in which its liquid and gaseous states are indistinguishable from one another. For carbon dioxide, the critical temperature is about 31 degrees C. (88 degrees D) and the critical pressure is about 73 atmospheres or about 1070 psi.

The term "supercritical carbon dioxide" as used herein refers to carbon dioxide at a temperature greater than about 31 degrees C. and a pressure greater than about 1070 psi. Liquid carbon dioxide may be obtained at temperatures of from about −15 degrees C. to about −55 degrees C. and pressures of from about 77 psi to about 335 psi. One or more solvents and blends thereof may optionally be included in the carbon dioxide. Illustrative solvents include, but are not limited to, tetrafluoroisopropanol, chloroform, tetrahydrofuran, cyclohexane, and methylene chloride. Such solvents are typically included in an amount, by weight, of up to about 20%.

In general, carbon dioxide may be used to effectively lower the glass transition temperature of a polymeric material to facilitate the infusion of pharmacological agent(s) into the polymeric material. Such agents include but are not limited to hydrophobic agents, hydrophilic agents and agents in particulate form. For example, following fabrication, an endoprosthesis and a hydrophobic pharmacological agent may be immersed in supercritical carbon dioxide. The supercritical carbon dioxide "plasticizes" the polymeric material, that is, it allows the polymeric material to soften at a lower temperature, and facilitates the infusion of the pharmacological agent into the polymeric endoprosthesis or polymeric coating of a stent at a temperature that is less likely to alter and/or damage the pharmacological agent.

As an additional example, an endoprosthesis and a hydrophilic pharmacological agent can be immersed in water with an overlying carbon dioxide "blanket". The hydrophilic pharmacological agent enters solution in the water, and the carbon dioxide "plasticizes" the polymeric material, as described above, and thereby facilitates the infusion of the pharmacological agent into a polymeric endoprosthesis or a polymeric coating of an endoprosthesis.

As yet another example, carbon dioxide may be used to "tackify", or render more fluent and adherent a polymeric endoprosthesis or a polymeric coating on an endoprosthesis to facilitate the application of a pharmacological agent thereto in a dry, micronized form. A membrane-forming polymer, selected for its ability to allow the diffusion of the pharmacological agent therethrough, may then applied in a layer over the endoprosthesis. Following curing by suitable means, a membrane that permits diffusion of the pharmacological agent over a predetermined time period forms.

Objectives of therapeutics substances incorporated into materials forming or coating an endoprosthesis according to the invention include reducing the adhesion and aggregation of platelets at the site of arterial injury, block the expression of growth factors and their receptors; develop competitive antagonists of growth factors, interfere with the receptor signaling in the responsive cell, promote an inhibitor of smooth muscle proliferation. Antiplatelets, anticoagulants, antineoplastics, antifibrins, enzymes and enzyme inhibitors, antimitotics, antimetabolites, anti-inflammatories, antithrombins, antiproliferatives, antibiotics, and others may be suitable. More specific examples of the foregoing examples are set forth in related Provisional Patent Application Ser. No. 60/426,125, and are incorporated herein.

Details of the invention can be better understood from the following descriptions of specific embodiments according to the invention. As an example, in FIG. 1, distal end 3 of standard delivery catheter 1 is shown, bearing endoprosthesis 10. Although an endoprosthesis according to the invention may be self-expanding, endoprosthesis 10 mounted on distal end 3 is balloon-expandable. Accordingly, endoprosthesis 10 is deployed via delivery catheter 1, which comprises balloon 5 at distal end 3. Endoprosthesis 10 may be fabricated from one or more of the foregoing conventional or shape memory materials, polymers, or other suitable materials selected for molecular weight, chemical composition and other properties, manufactured to achieve any desired geometries and processed to achieve sterilization, desired geometries and in vivo lifetime. Endoprosthesis 10 is "crimped" down upon balloon 5 into its low-profile delivery configuration. Endoprosthesis 10 can then be tracked to a lesion site within a lumen of the body where endoprosthesis 10 can be deployed. In order to deploy endoprosthesis 10, balloon 5 is inflated via inflation medium through catheter 1. The outward radial force of expanding balloon 5 expands endoprosthesis 10 to its deployed configuration, and permanently plastically deforms endoprosthesis 10 to exert an outward radial force upon the diseased lumen.

Figure 2:
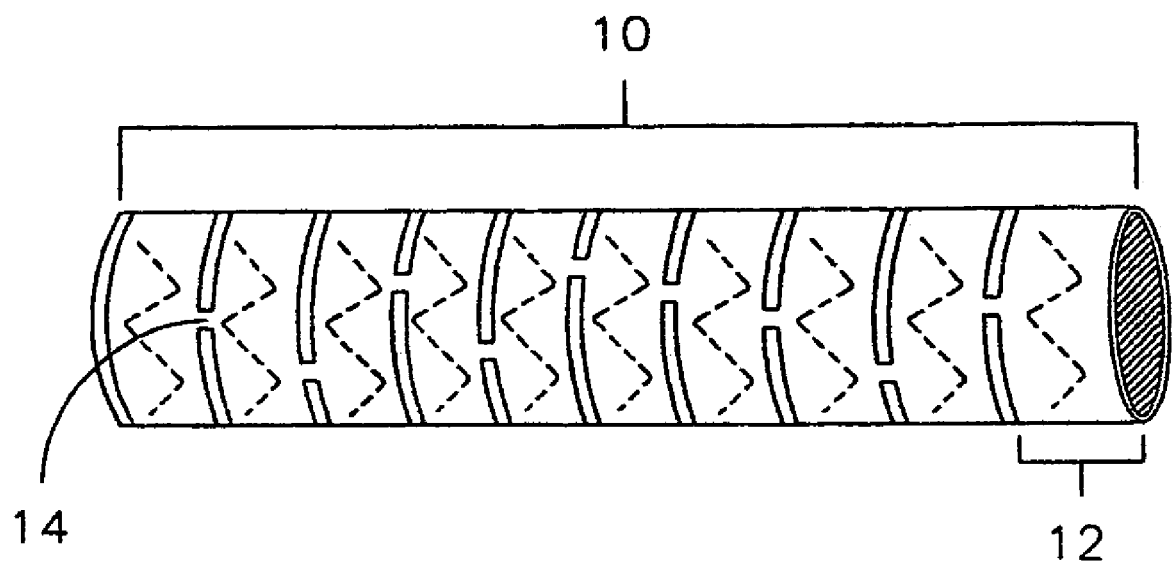
FIG. 2 shows the embodiment of FIG. 1 in its deployed configuration.

FIG. 2 illustrates endoprosthesis 10. Accordingly, endoprosthesis 10 may be between 0.5 mm and 10.0 mm at its deployed diameter, depending upon the size of the lumen of the patient (not pictured). Endoprosthesis 10 comprises support elements 12 and one or more connecting elements 14.

Figure 3A:
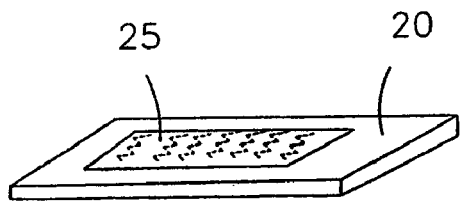
FIGS. 3A-C illustrate a method of manufacture according to the invention.
Figure 3B:
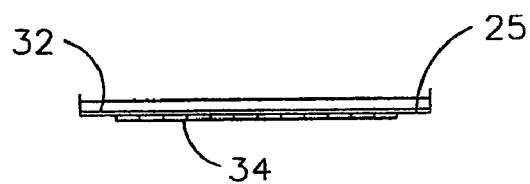
Figure 3C:
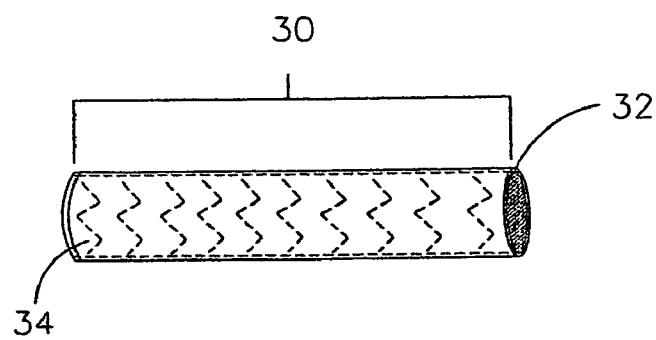

The manufacture of an endoprosthesis according to the invention can be better understood from a discussion of FIG. 3A-C. FIG. 3A represents an end view of mold 20. As a first step in preparing an endoprosthesis according to the invention, a blend of poly-1-lactide and poly-caprolactone in a ratio of between 80:20 and 95:5 is attained. Raw material is placed onto mold 20, heated and pressurized to produce flat cast film 25. Flat cast film 25 is removed from mold 20, as shown in FIG. 3B, and rolled to form endoprosthesis 30, shown in a plan view in FIG. 3C. Endoprosthesis 30, which is balloon-expandable, comprises thin film portion 32 and one or more ribs 34. Alternatively, thin film portion 32 can be removed at all but portions left to connect ribs to one another. Also, in an alternative embodiment, one or more therapeutic agents can be added to polymer mixture such that the resulting endoprosthesis elutes one or more therapeutic agents in situ.

Figure 4A:
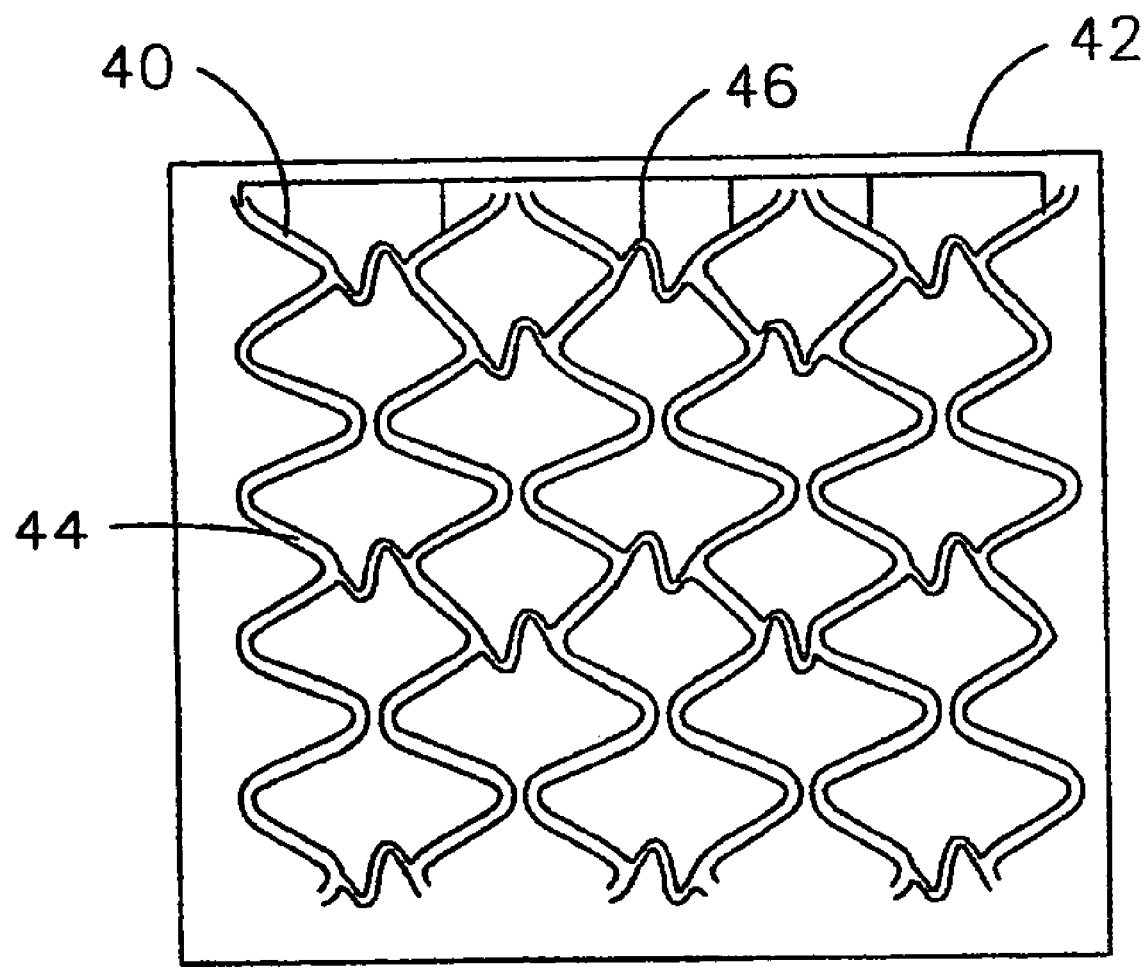
FIGS. 4A-4C illustrate successive steps in the manufacture of an embodiment according to the invention.
Figure 4B:
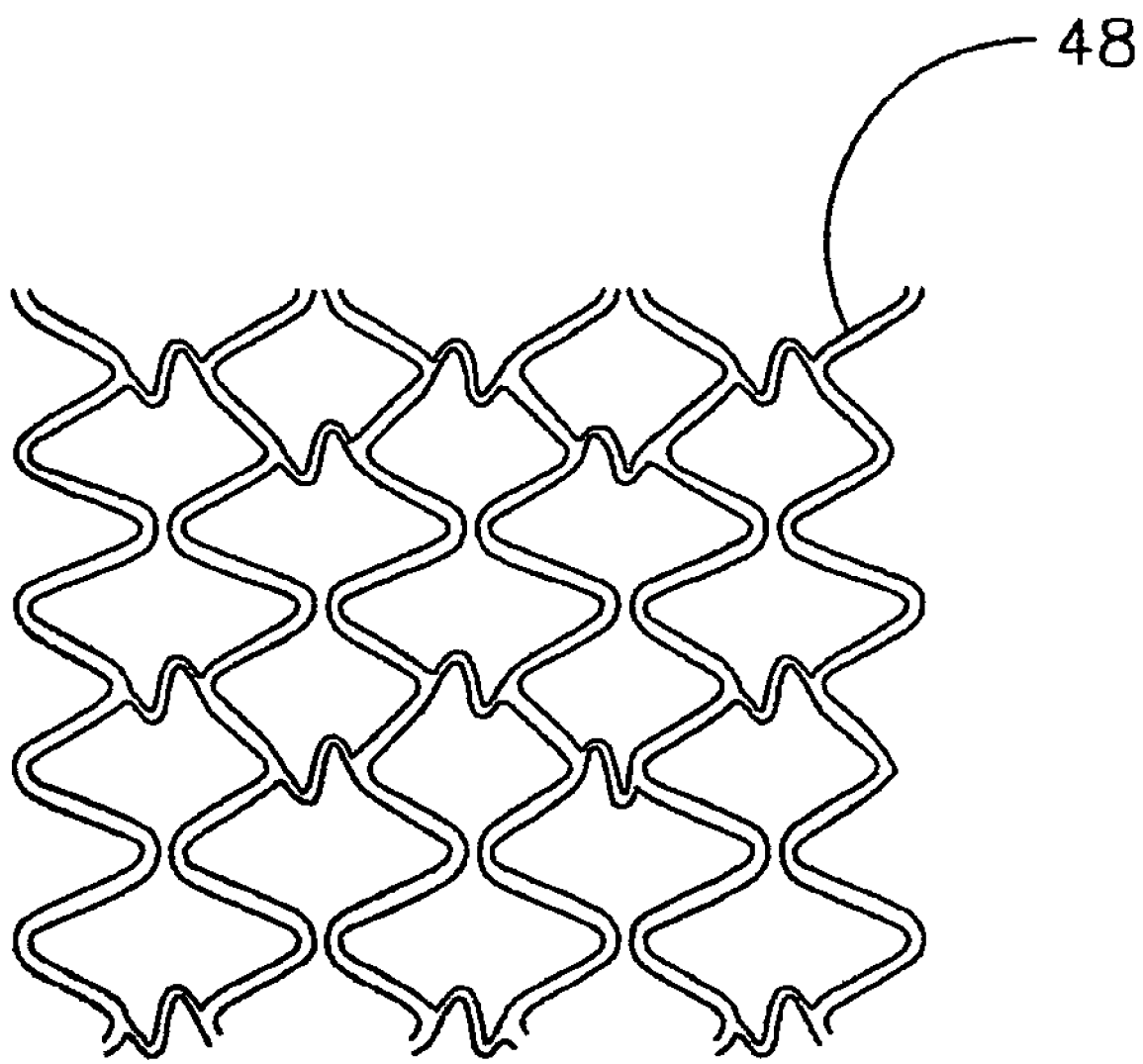
Figure 4C:
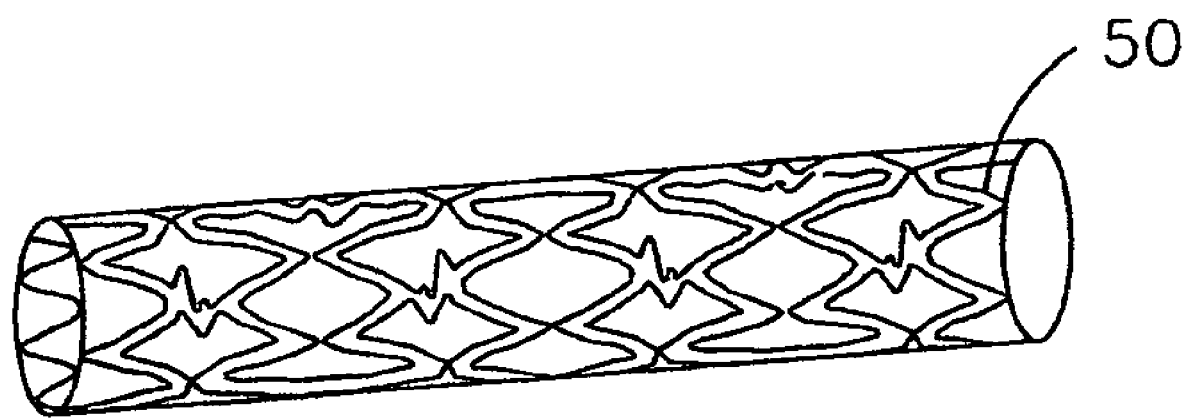

An alternative embodiment according to the invention may be described in relation to FIG. 4A-C. FIG. 4A is a plan view depicting mold 40, etched onto flat plate 42. Mold 40 comprises relief for endoprosthesis elements 44, and connecting members 46. As a first step in fabricating an endoprosthesis using mold 40, polymers having desired properties are placed onto mold 40, heated and pressurized to form flat cast film 48, shown in FIG. 4B. Flat cast film 48 is removed from mold 40, trimmed of excess via laser technology known in the art, including but not limited to excimer laser at a wavelength between 150 nm and 250 nm, or carbon dioxide laser, and rolled to form endoprosthesis 50, shown in FIG. 4C. Although a self-expanding alternative is possible, endoprosthesis 50 is balloon expandable. An endoprosthesis according to the invention may alternatively be fabricated using injection molding, compression molding, or by laser cutting a tube, or chemically etching a tube.

Figure 5A:
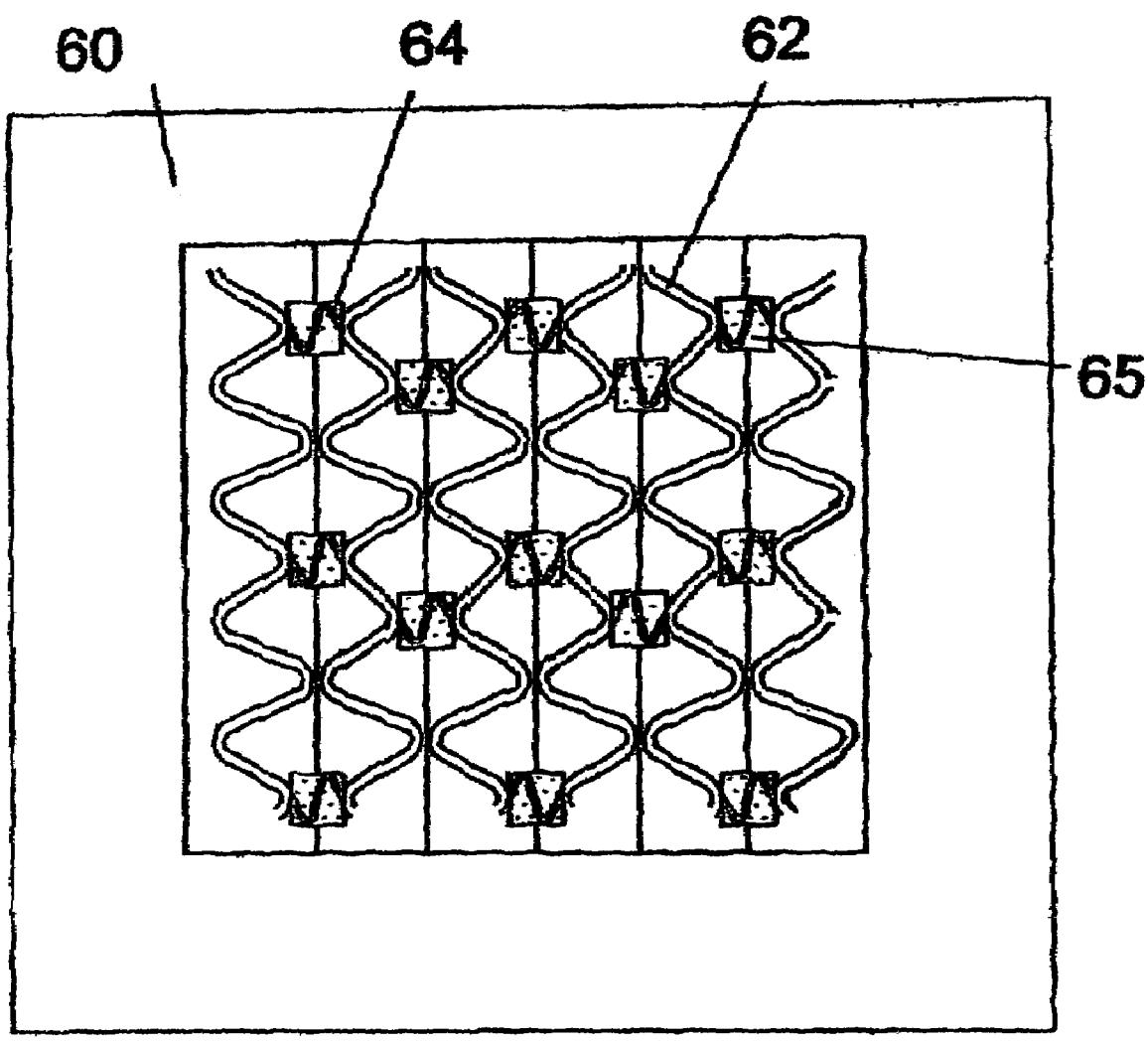
FIGS. 5A-5D illustrate an alternative method according to the invention.
Figure 5B:
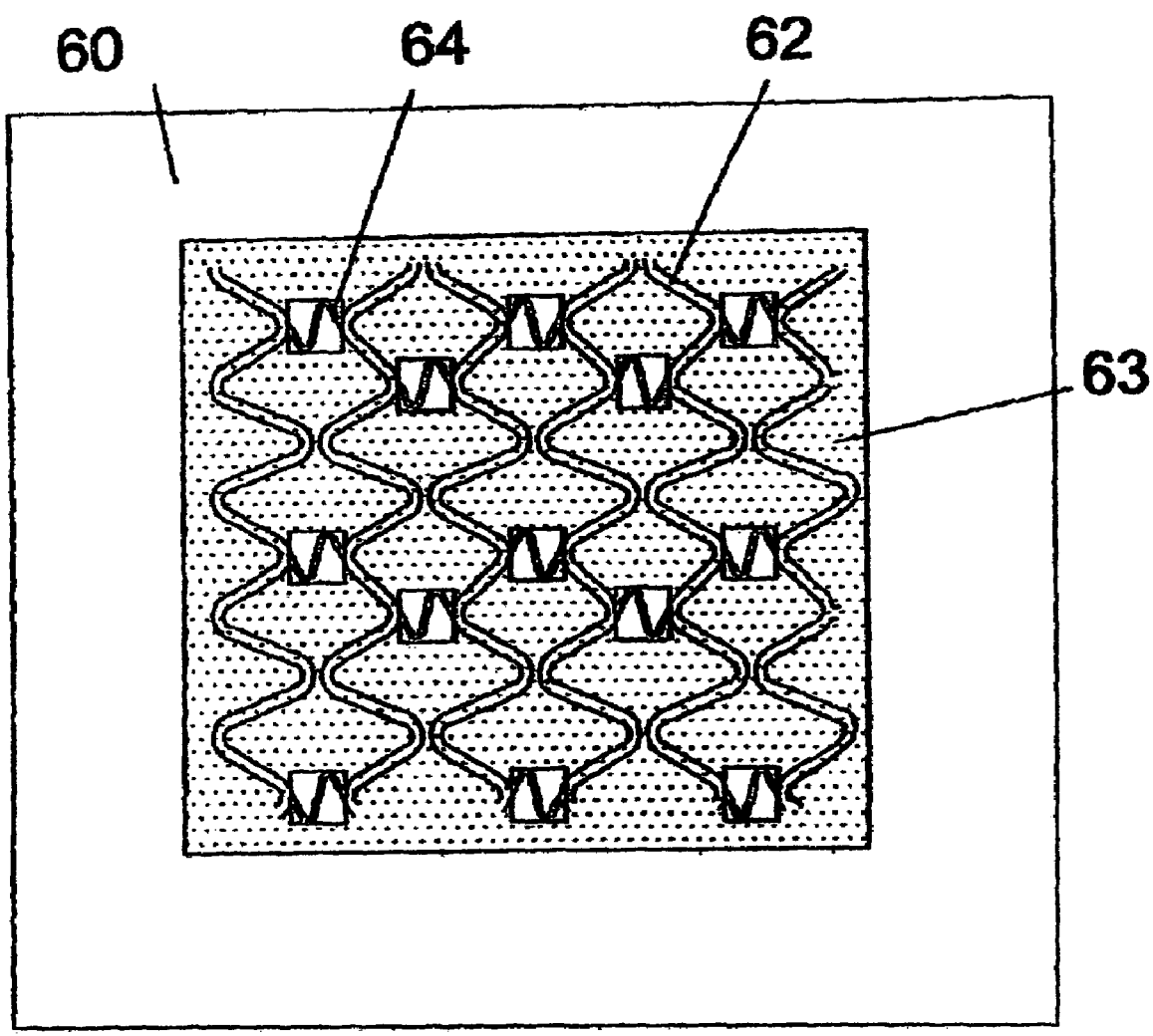
Figure 5C:
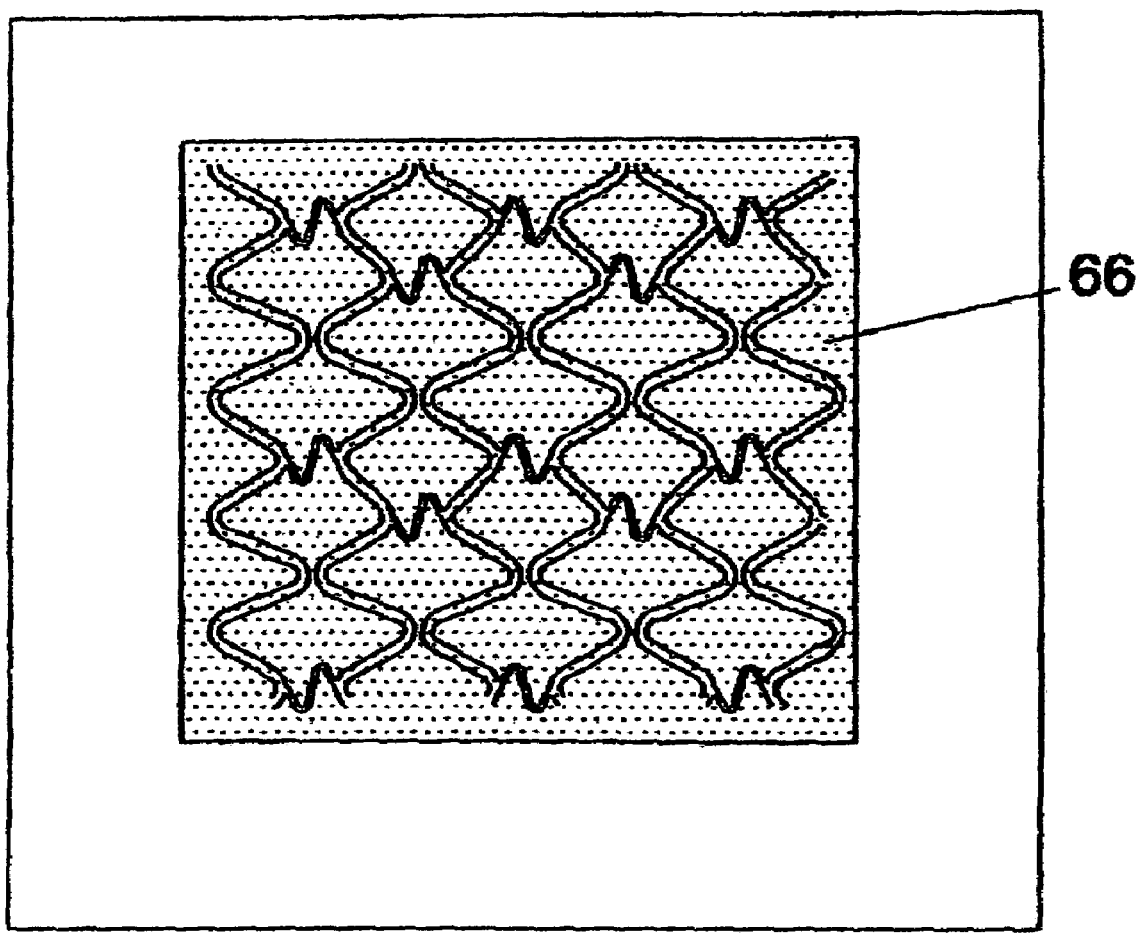
Figure 5D:
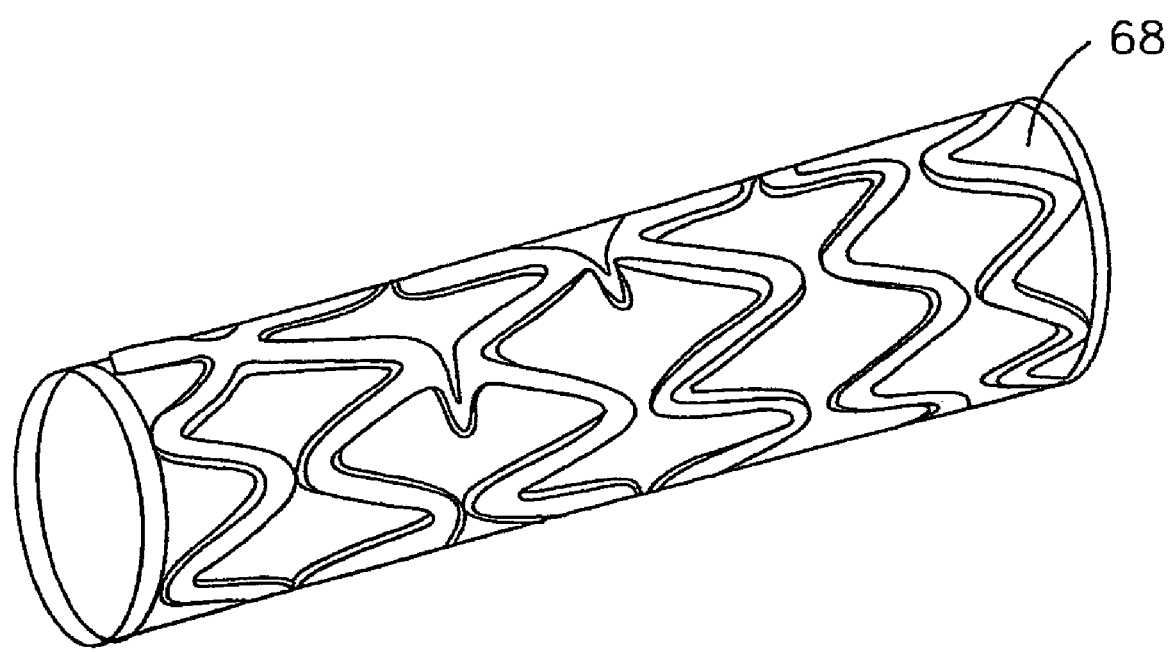

Yet another alternative embodiment according to the invention is illustrated in FIGS. 5A-C. Mold 60 of FIG. 5A comprises relief for endoprosthesis elements 62 and connecting elements 64. In a first step, suitable "masking" material 65 is placed over etchings for connecting elements 64 before a desired selection of endoprosthesis materials, chosen to confer desired physical properties upon the resulting endoprosthesis elements, are placed onto mold 60, heated and pressurized, preventing the formation of connecting elements during the first step. Following the formation of endoprosthesis elements 62, masking material 65 is removed, leaving endoprosthesis elements 62 covered in a first thin film 63, as shown in FIG. 5B. A second selection of desired endoprosthesis materials, chosen to confer desired physical properties to be conferred upon the resulting connecting elements, is then placed onto mold 60, heated and pressurized, to form composite flat film 68, shown in FIG. 5C. In the alternative, a masking material may be placed over endoprosthesis elements 62. Following forming, composite flat film 66 is removed from mold 60, trimmed of excess and rolled to form composite endoprosthesis 68, shown in FIG. 5D.

Alternatively, other regions of the endoprosthesis, for example, the end regions, may be formed selectively from yet a third polymeric composition in order to confer desired physical properties on the resulting end regions. The luminal surface of the endoluminal prosthesis is another example of a region of an endoprosthesis may be selectively formed from a particular polymeric composition. Physical properties that can be controlled according to the invention include but are not limited to density, modulus of elasticity, degree of crystallinity, permeability and diffusion coefficient.

Figure 6:
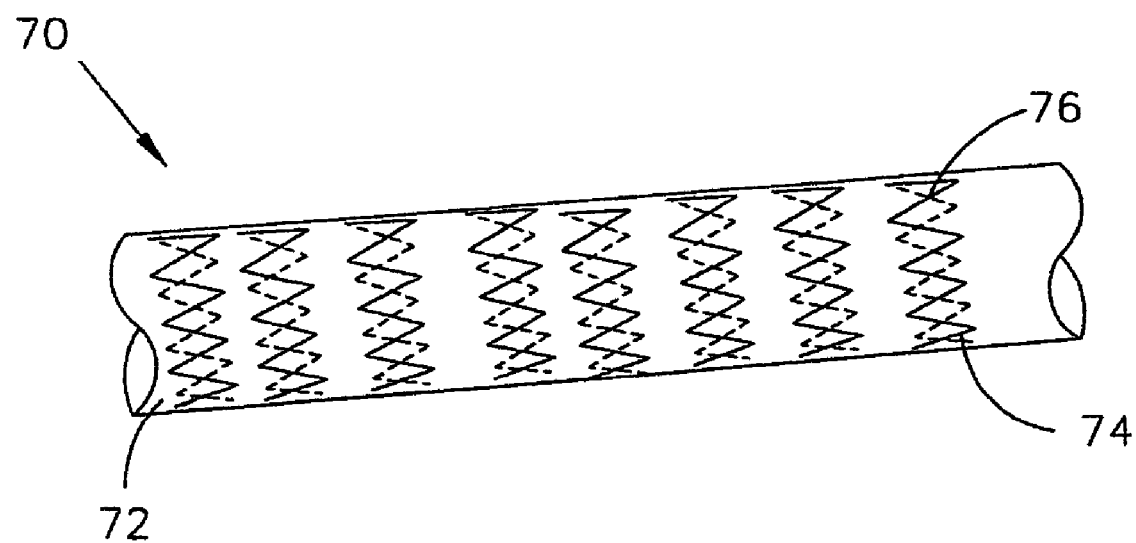
FIG. 6 depicts an alternative embodiment according to the invention.

Turning now to FIG. 6, another embodiment according to the invention is provided. Endoprosthesis 70 comprises highly compliant tubular member 72 enveloping a rigid thin fiber 74. One or more plastically deformable bonds 76 is formed at the intersections of rigid thin fibers 74. Endoprosthesis 70 may be self-expanding, balloon assisted, or balloon expandable.

Figure 7:
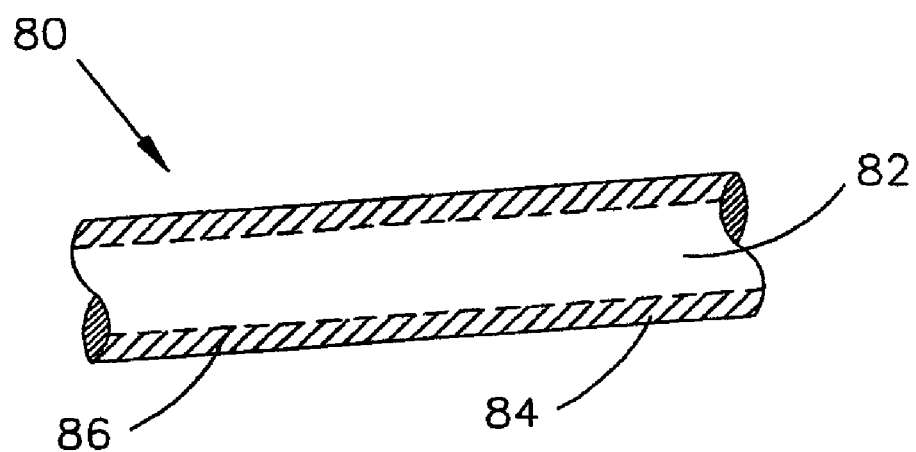
FIG. 7 illustrates yet another embodiment according to the invention.

An additional embodiment is illustrated in FIG. 7. Endoprosthesis 80 comprises a generally tubular member 82 that further encapsulates cavity 84. Cavity 84 is filled with a suitable curable material 86. Following deployment by balloon expansion, curable material 86 cures to impart rigidity to endoprosthesis 80.

Figure 8:
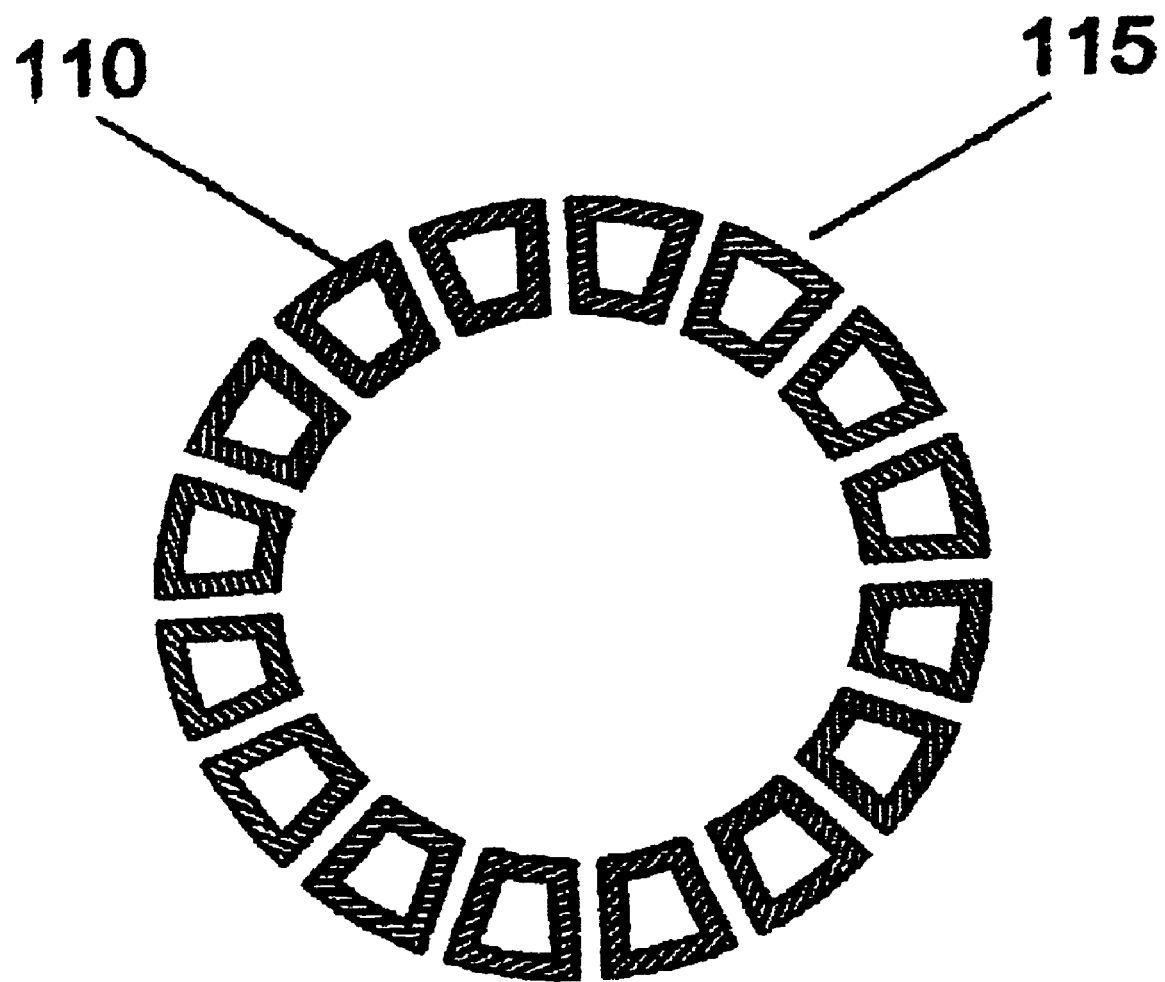
FIG. 8 illustrates an additional embodiment according to the invention.

FIG. 8 illustrates an end view of alternative embodiment of the invention comprising layer 110 into which a hydrophilic therapeutic agent has been incorporated. Following fabrication of endoprosthesis 115 according to any of the methods described herein from any of suitable material, endoprosthesis 115 is immersed in a solution of polymer, water and hydrophilic therapeutic agent, underlying a "blanket" of supercritical carbon dioxide. The carbon dioxide renders the polymer more receptive to the incorporation of therapeutic agent. The polymer comprising the therapeutic agent forms layer 110 on the surface of endoprosthesis 115 for elution in situ.

Figure 9:
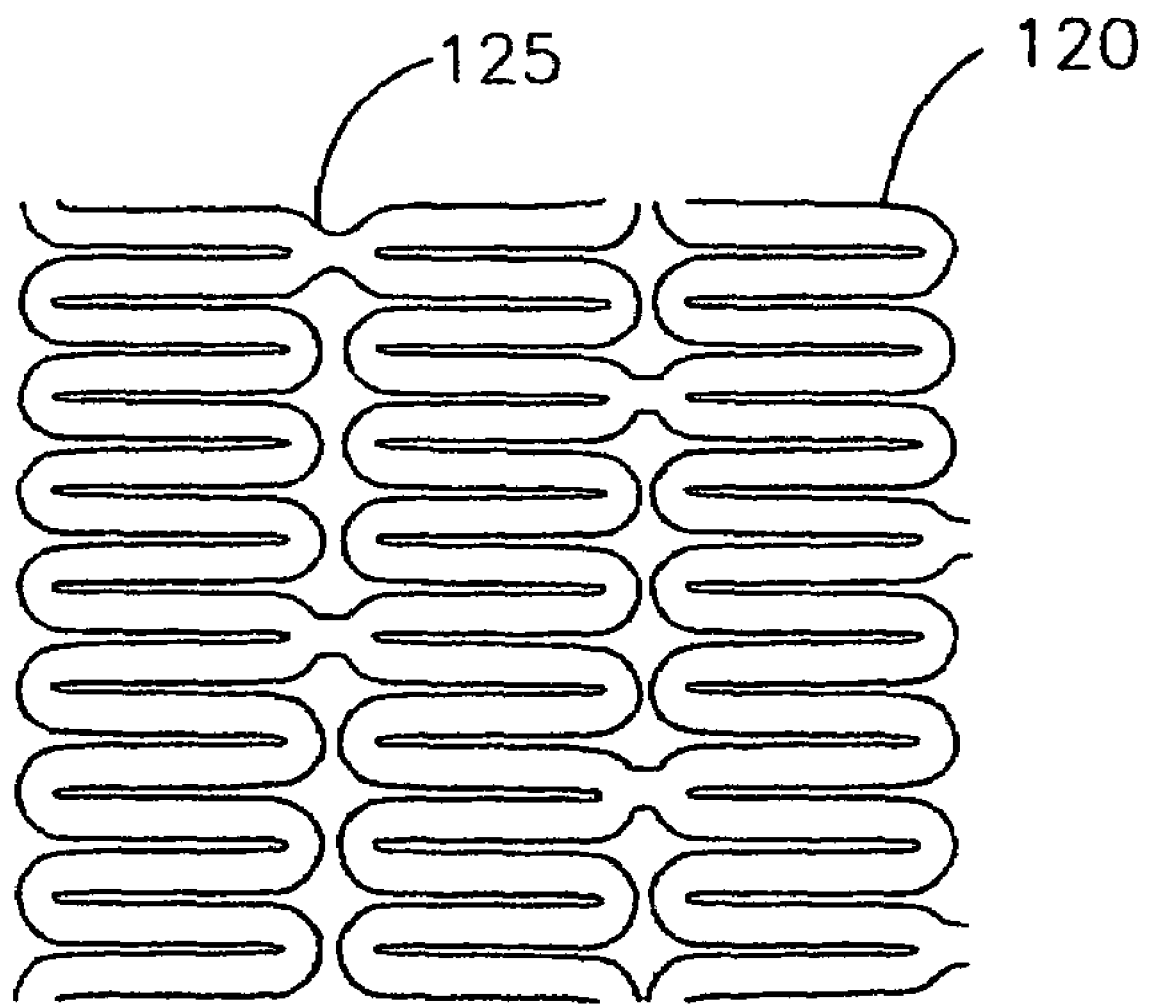
FIG. 9 is a plan view of an embodiment according to the invention.

Turning now to FIG. 9, a portion of an element of an endoprosthesis according to the invention is illustrated as a flat section. Endoprosthesis elements 120 are generally serpentine, and between 0.008 and 0.010 inches wide. Two opposed connecting members 125 are disposed between endoprosthesis elements and are spaced spirally at 45 degrees. FIG. 10A represents an end view of a cross-section taken along the longitudinal axis of endoprosthesis 126 according to the invention. Endoprosthesis elements 127 comprise trapezoidal cross-sections, oriented such that the broadest side of the trapezoid is disposed at the outer diameter, or vascular surface of endoprosthesis 126. Such a cross section maximizes the vascular surface area of endoprosthesis 126 by over 20% as compared to an equivalent cross sectional area, while allowing endoprosthesis 126 to be crimped down to a minimal profile for tracking and delivery through the vasculature. Endoprosthesis 126 may be excimer laser cut from a cylinder, and endoprosthesis elements 127 can accordingly be cut to exhibit a trapezoidal cross-section. FIG. 10B illustrates an end view of a cross section of a prior art endoprosthesis comprising elements 128 having generally rectangular cross-sections.

Figure 11:
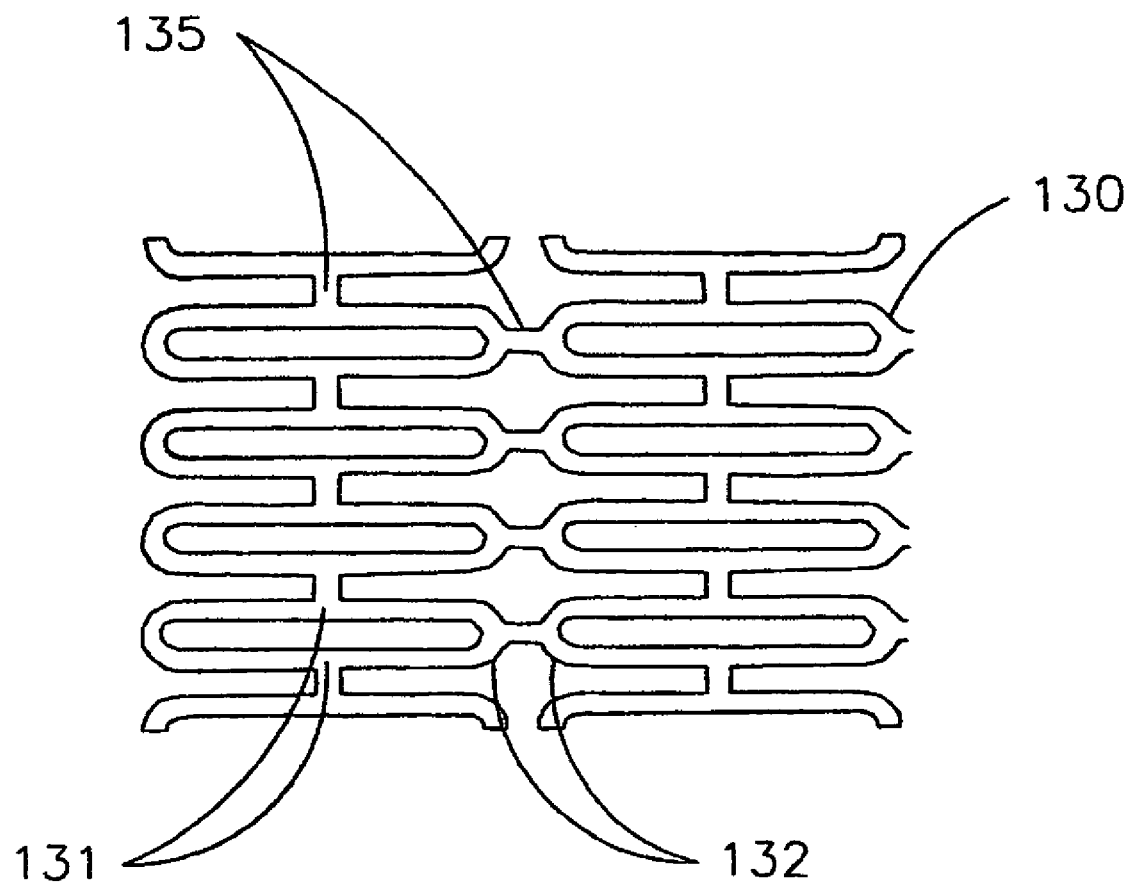
FIG. 11 is a plan view of an alternative embodiment according to the invention.

In FIG. 11, endoprosthesis element 130 is generally elliptical or ovular in shape. Connecting members 135 adjoin each adjacent endoprosthesis element 130 generally at the midsections 131 and ends 132 of endoprosthesis elements 130. Endoprosthesis elements 130 may be fabricated from a first material exhibiting a high modulus of elasticity and strength, while connecting members 135 may be fabricated from a second, more flexible material, such as an elastomer.

Figure 12:
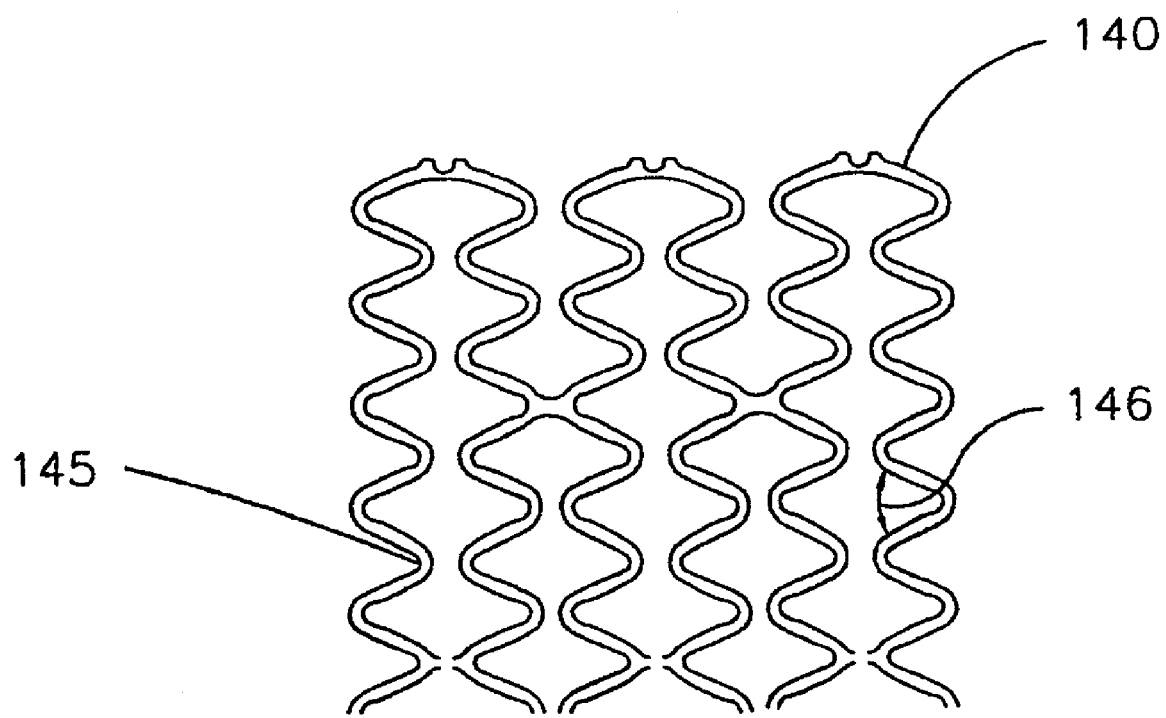
FIG. 12 is a plan view of an alternative embodiment according to the invention.

FIG. 12 depicts a portion of an element to be used in the fabrication of an alternative embodiment according to the invention in a partially expanded or deployed configuration. Endoprosthesis members 140 comprise a thinner cross-section at the inner apex 145 to allow for preferential bending at inner apex 145 upon expansion. Such preferential bending enhances uniform deployment of an endoprosthesis. Included angle 146 is between 40 and 65 degrees. Upon expansion, strain induced crystallization is induced in the polymer at the bending site, increasing the degree of crystallization, and consequently the strength of the material, at the bending site.

Figure 13A:
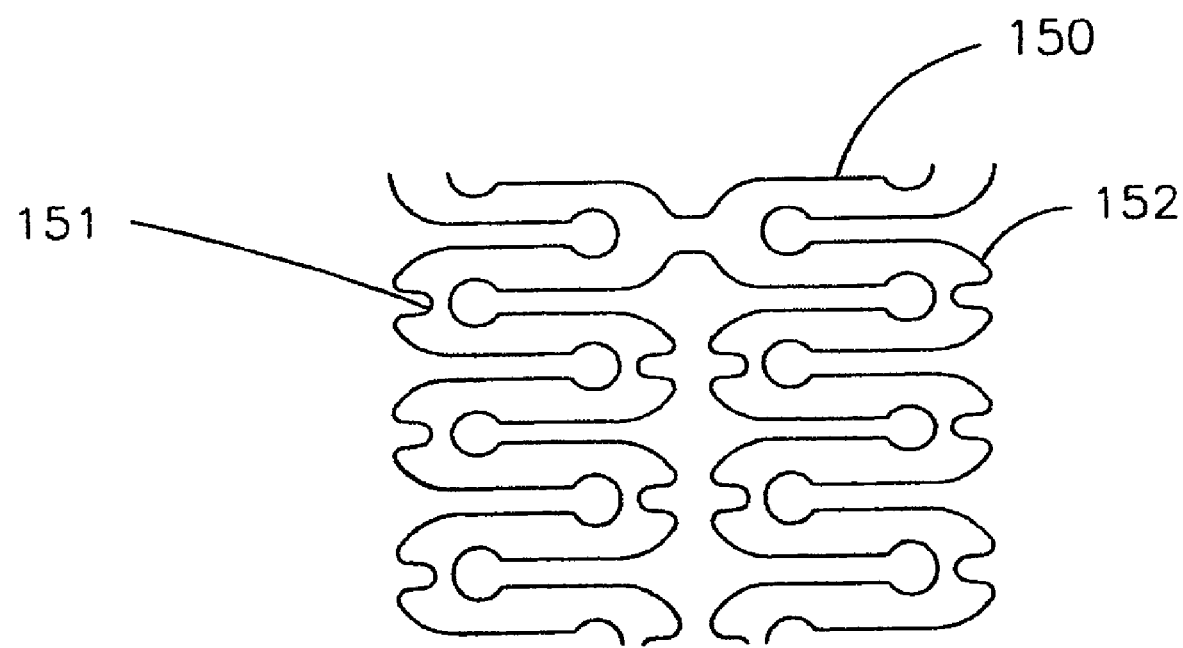
FIG. 13A is a plan view of another alternative embodiment according to the invention.
Figure 13B:
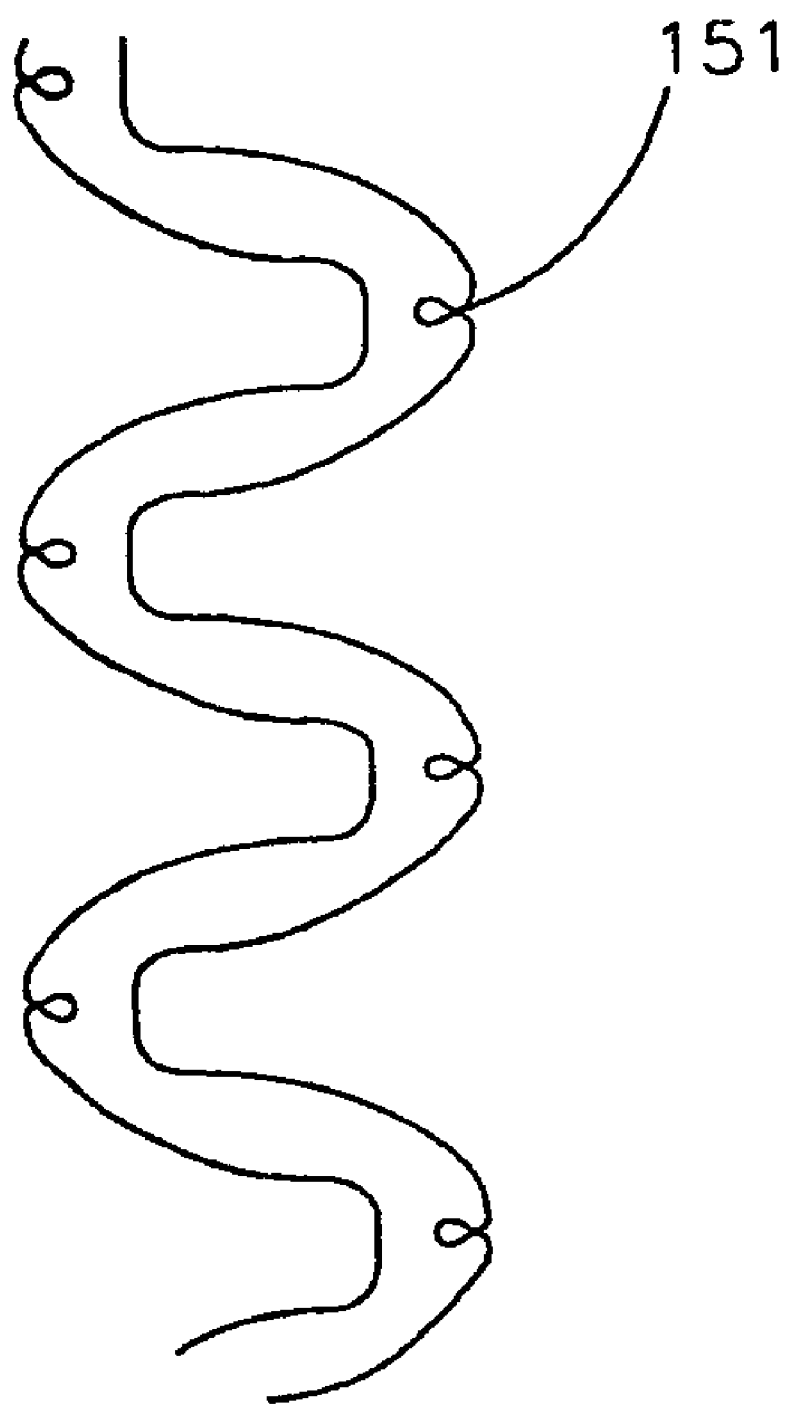
FIG. 13B is a plan view of a portion of the element of FIG. 13A illustrating the reconfiguration of the element when in its deployed configuration.

FIG. 13A illustrates a portion of an alternative embodiment according to the invention wherein generally serpentine endoprosthesis elements 150 comprise deployment stops 151 at one or more apex 152. As illustrated in FIG. 13B, once expansion of the endoprosthesis reaches a certain point, the edges of deployment stops 151 touch one another and prevent further expansion of that element and force expansion of the next element, thus ensuring uniform expansion.

Figure 14A:
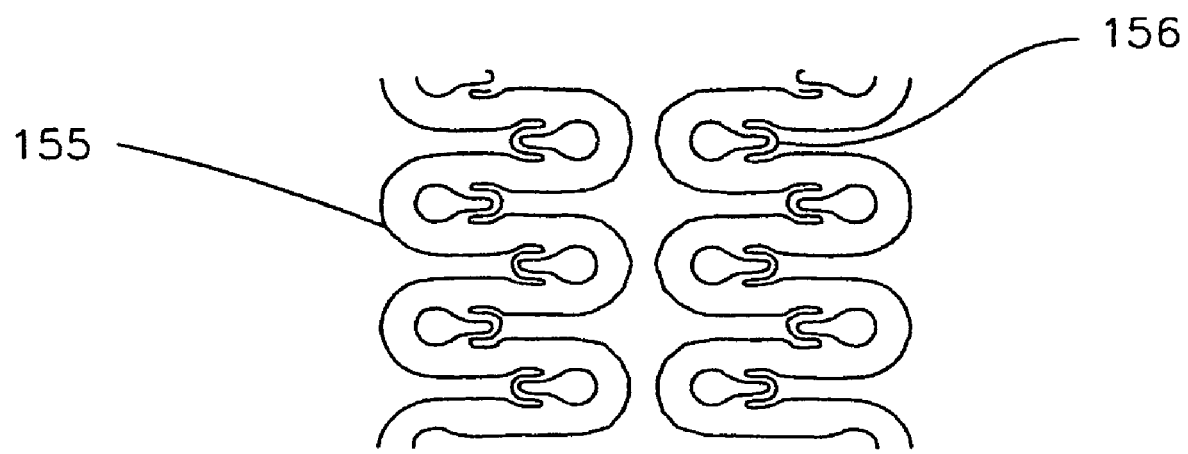
FIG. 14A is a plan view of yet another alternative embodiment according to the invention.
Figure 14B:
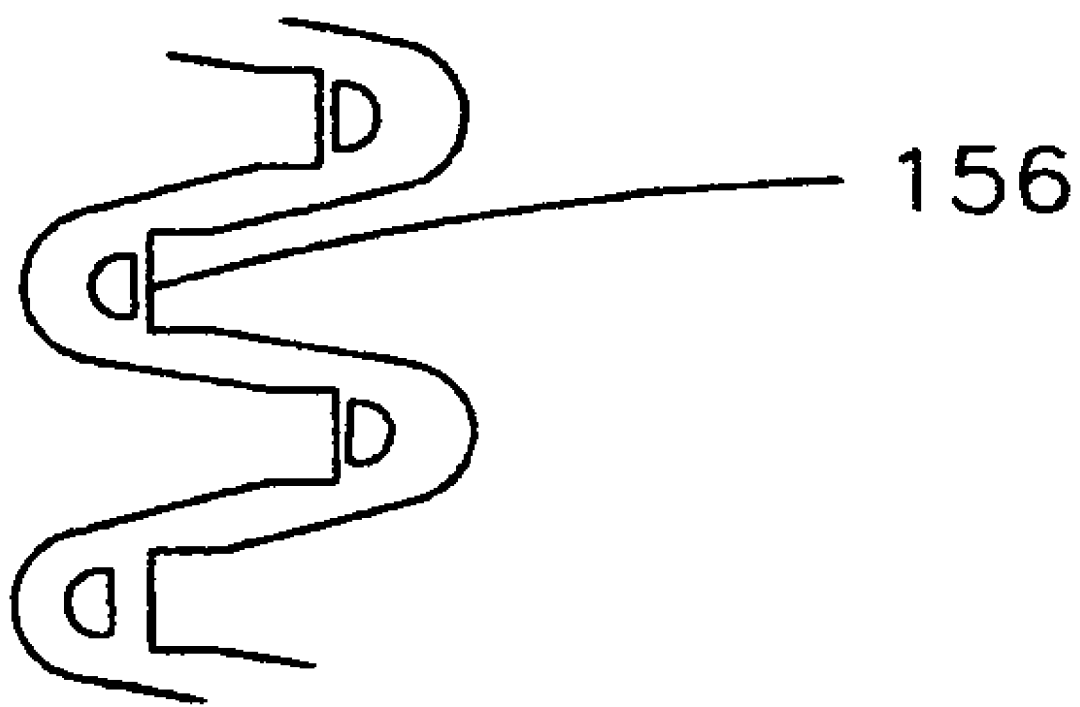
FIG. 14B is a plan view of a portion of the element of FIG. 14A illustrating the reconfiguration of the element when in its deployed configuration.

FIG. 14A illustrates yet another embodiment according to the invention prior to expansion. FIG. 14B illustrates a portion of the embodiment of FIG. 14A after expansion. Endoprosthesis elements 155 comprise deployment stops 156 inside each crown element 157. Upon reaching a linear shape as shown in FIG. 14B, deployment stops 156 prevent further expansion of that element and force expansion of the next element, thus ensuring uniform expansion.

Figure 15:
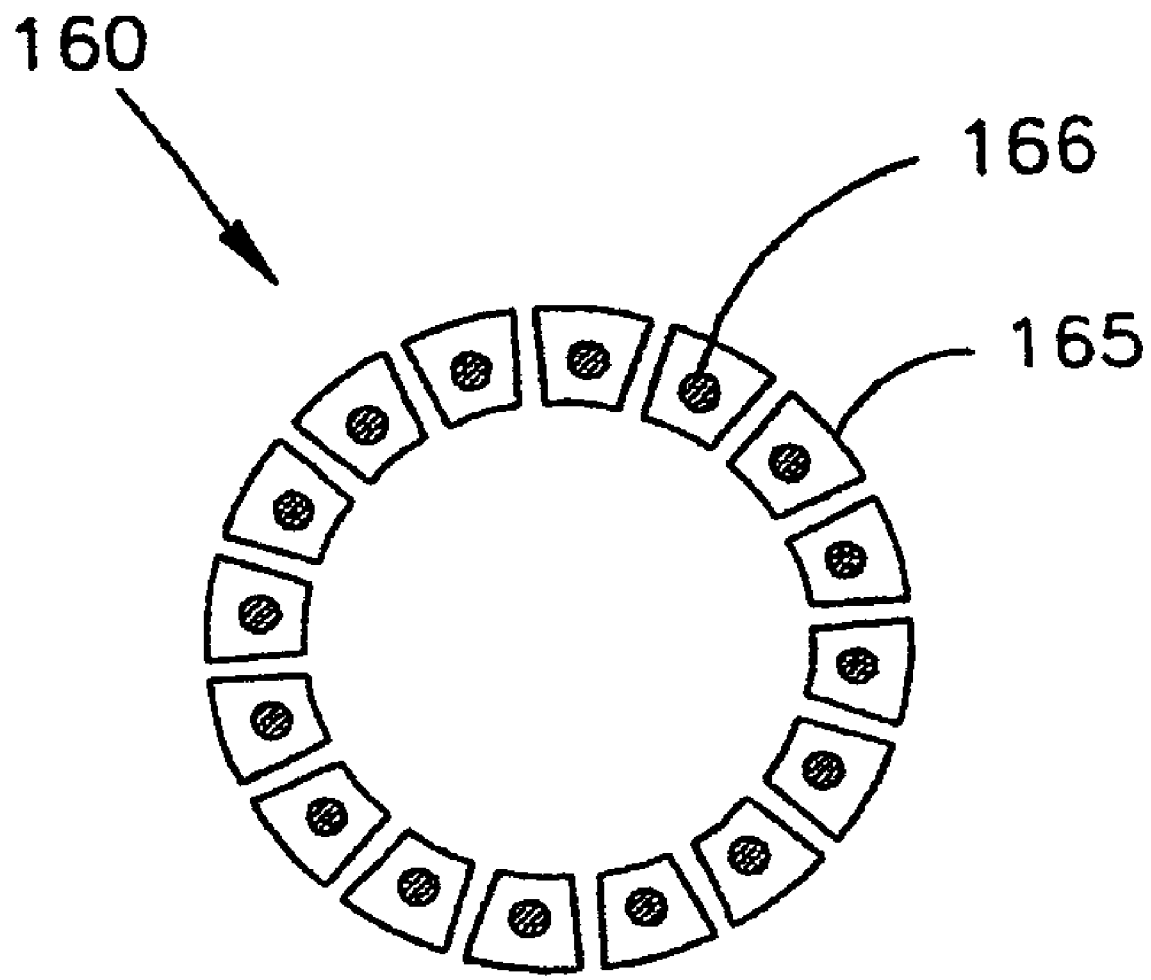
FIG. 15 is an end view of a cross section of yet another embodiment according to the invention.

An alternative embodiment according to the invention is illustrated in a cross section of an endoprosthesis 160 shown in FIG. 15. Endoprosthesis elements 165, of a trapezoidal shape, comprise metal reinforcement elements 166. Metal reinforcement element 166 may be fabricated from any suitable biocompatibly corrosive metal, such as, for example, Magnesium. This composite can greatly enhance the mechanical performance of the device.

Figure 16:
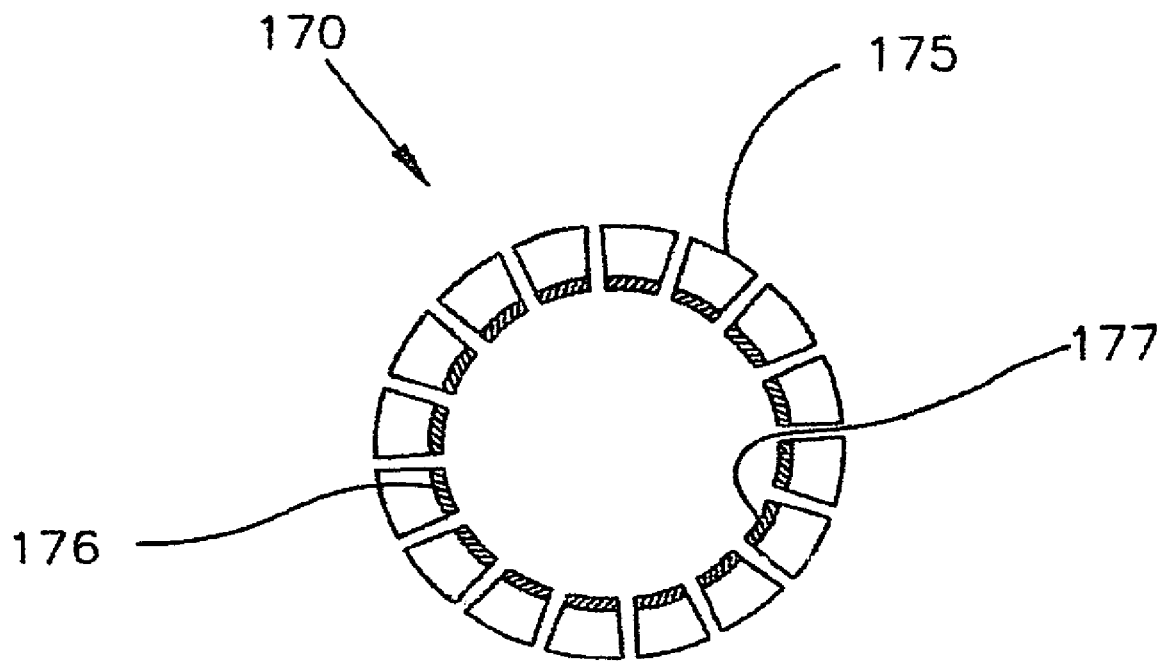
FIG. 16 is an end view of a cross section of yet another embodiment according to the invention.
Figure 17:
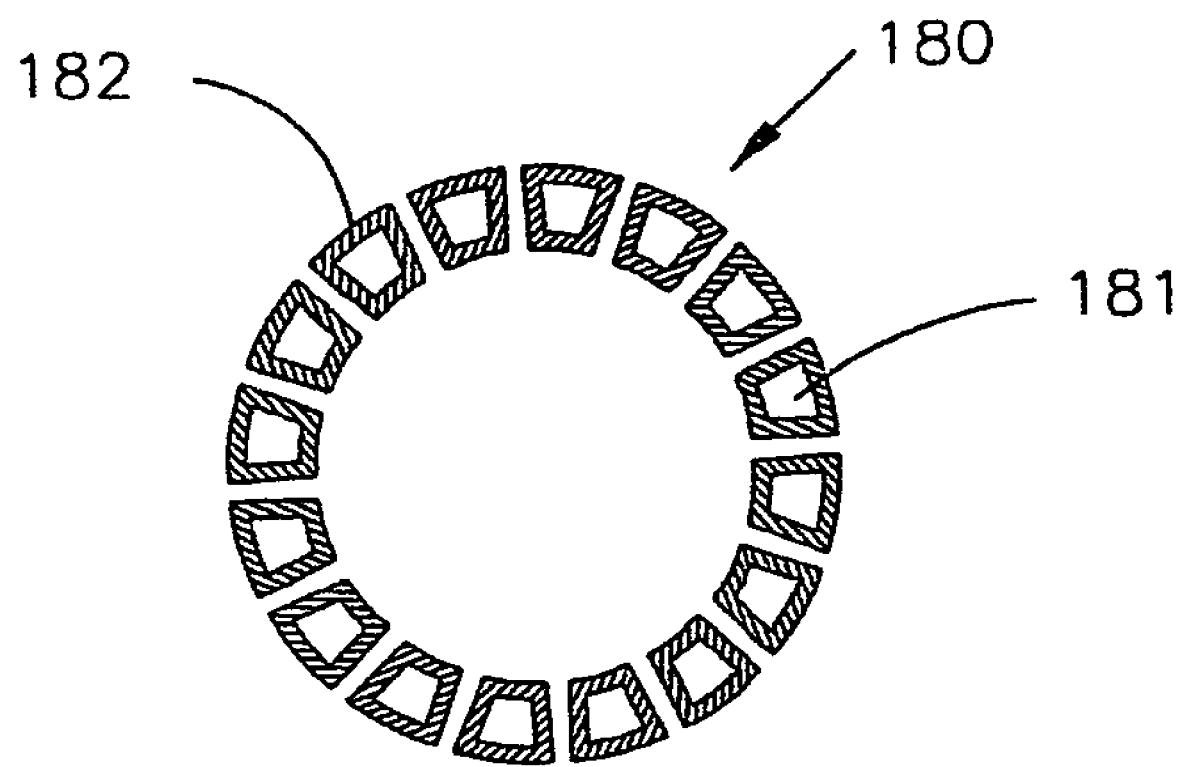
FIG. 17 is an end view of a cross section of yet another embodiment according to the invention.

FIG. 16 depicts a cross section of endoprosthesis 170. Endoprosthesis elements 175 comprise metal reinforcement layer 176 disposed on luminal surface 177 of endoprosthesis 170. Similar to the metal reinforcement elements 166 depicted in FIG. 15, metal reinforcement layer 176 may comprise any suitable biocompatibly corrosive metal. FIG. 17 illustrates a cross section of endoprosthesis 180. Endoprosthesis elements 181 are encapsulated by metal reinforcement layer 182, which may comprise any suitable biocompatibly corrosive metal. This encapsulation may be spray-coated, dipped, electrostatically coated, ion beam deposited or coated by any means known by those skilled in the art.

Figure 18:
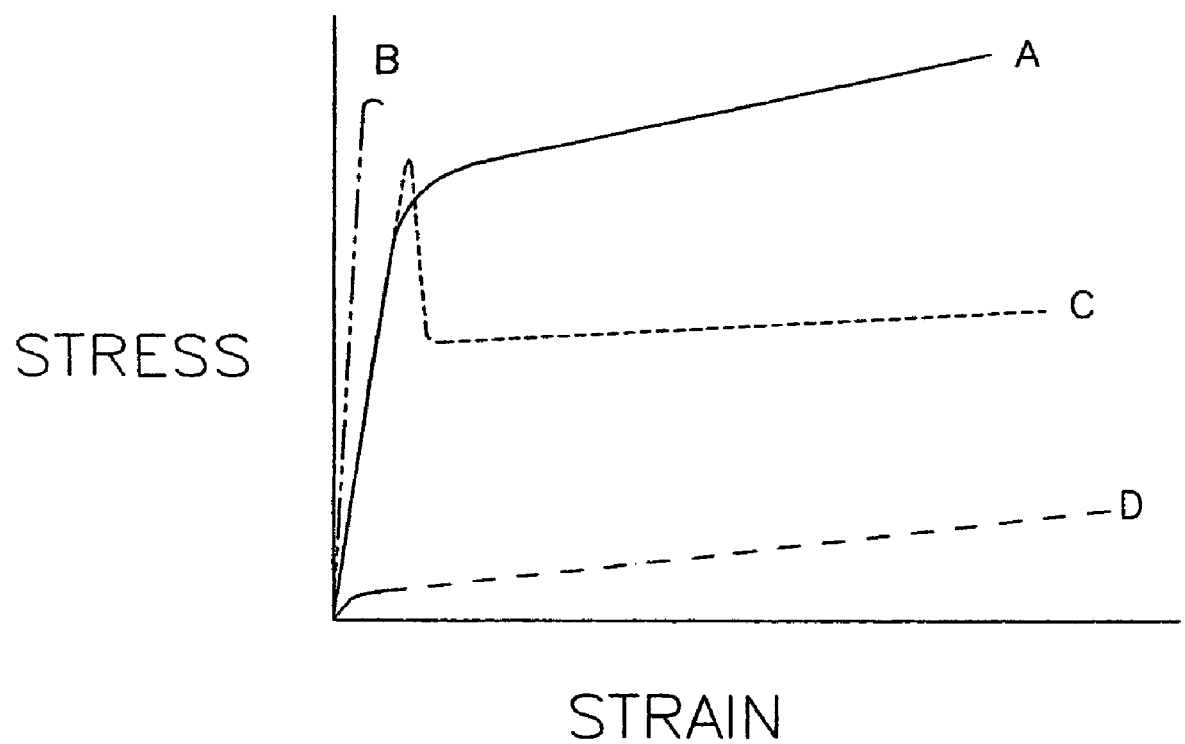
FIG. 18 is a graph illustrating the modulus of elasticity of prior art materials and materials according to the invention.

Turning now to FIG. 18, the stress-strain curve exhibited by materials according to the invention is curve A. The engineering tensile stress strain curve was obtained by static loading of the material, that is, by applying the load slowly enough that all parts of the material are in equilibrium at any instant. For most engineering materials, the curve will have an initial linear region in which deformation is reversible and time independent. The slope in this region is Young's modulus. The proportional elastic limit is the point where the curve starts to deviate from a straight line. The elastic limit is the point on the curve beyond which plastic deformation is present after release of the load. If the stress is increased further, the stress strain curve departs more and more from the straight line. In FIG. 18, the curve for a brittle material is indicated at B. A typical copolymer trend is expressed in curve C, and for a low modulus material in curve D. Curve A closely resembles the stress-strain curve of a stainless steel alloy, radically surpassing the performance of know polymers under stress.

According to the invention, a poly-1-lactide blend with poly-caprolactone in a ratio of between 80:20 and 95:5 is preferred. A material prepared comprising the foregoing ratio of polymers consistently achieves the modulus of elasticity illustrated as curve A in FIG. 18. The shape of this curve mirrors that obtained by biometals such as 316 L, stainless steel, a material commonly used in vascular stents. Further, if the mixture is annealed at roughly 100 degrees C. in an inert, moisture-free environment for between 1 and 24 hours, and most desirably between 1 and 3 hours, polymer chain crystallization is enhanced, and consequently the point at which plastic deformation occurs is increased. Still further, upon deployment, strain induced crystallization is initiated, further raising the point on the curve at which plastic deformation occurs.

While particular forms of the invention have been illustrated and described above, the foregoing descriptions are intended as examples, and to one skilled in the art will it will be apparent that various modifications can be made without departing from the spirit and scope of the invention.

We claim:
1. A bioabsorbable, magnesium-reinforced polymeric endoprosthesis comprising an expandable cylindrical body formed from at least one erodible polymer having one or more endoprosthesis support elements fabricated therefrom, wherein said erodible polymer confers sufficient radial strength upon the endoprosthesis support element in order for the endoprosthesis to restore fluid flow through a diseased lumen, and said one or more endoprosthesis support elements further includes at least one reinforcing element comprising magnesium,
  wherein said endoprosthesis comprises a luminal surface and a vascular surface, and said one or more endoprosthesis support elements define a central lumen along said luminal surface,
  wherein when a cross section is taken of an endoprosthesis support element from an end view, said endoprosthesis support element cross section comprises a trapezoidal shape, and
  wherein said reinforcing element encapsulates said one or more endoprosthesis support elements.

* * * * *